United States Patent
Mehta et al.

(10) Patent No.: US 10,946,002 B2
(45) Date of Patent: Mar. 16, 2021

(54) PHARMACEUTICAL SUSPENSION DOSAGE FORM OF BENZIMIDAZOLE COMPOUNDS AND PROCESS OF PREPARATION THEREOF

(71) Applicant: Jubilant Generics Limited, Uttar Pradesh (IN)

(72) Inventors: Kamal Surendrakumar Mehta, Noida (IN); Dinesh Kumar, Noida (IN); Saurabh Srivastava, Noida (IN); Basudev Paul, Noida (IN)

(73) Assignee: Jubilant Generics Limited

( * ) Notice: Subject to any disclaimer, the term of this patent is extended or adjusted under 35 U.S.C. 154(b) by 0 days.

(21) Appl. No.: 16/087,039

(22) PCT Filed: Oct. 6, 2017

(86) PCT No.: PCT/IB2017/056183
§ 371 (c)(1),
(2) Date: Sep. 20, 2018

(87) PCT Pub. No.: WO2018/065953
PCT Pub. Date: Apr. 12, 2018

(65) Prior Publication Data
US 2019/0216788 A1 Jul. 18, 2019

(30) Foreign Application Priority Data
Oct. 6, 2016 (IN) .............................. 201611034270

(51) Int. Cl.
*A61K 31/4439* (2006.01)
*A61P 1/04* (2006.01)
*A61K 9/16* (2006.01)
*A61K 9/28* (2006.01)
*A61K 9/00* (2006.01)

(52) U.S. Cl.
CPC ........ *A61K 31/4439* (2013.01); *A61K 9/0053* (2013.01); *A61K 9/2846* (2013.01); *A61P 1/04* (2018.01); *A61K 9/1623* (2013.01); *A61K 9/1652* (2013.01)

(58) Field of Classification Search
None
See application file for complete search history.

(56) References Cited

U.S. PATENT DOCUMENTS 5,817,338 A * 10/1998 Bergstrand ........... A61K 9/2081
424/468
2013/0273168 A1* 10/2013 Persson ................ A61K 9/0014
424/490

FOREIGN PATENT DOCUMENTS

WO WO-2013122554 A1 * 8/2013 ......... A61K 31/4439
WO WO-2017145146 A1 * 8/2017 ......... A61K 31/4439

OTHER PUBLICATIONS

Al-Gousous et al. "Toward biopredictive dissolution for enteric coated dosage forms," Molecular Pharmaceutics 13:1927-1936, 2016.*
Derwent abstract and machine translation, CN 106511280, printed 2019.*
Derwent abstract and machine translation, CN 105125517, printed 2019.*

* cited by examiner

*Primary Examiner* — David J Blanchard
*Assistant Examiner* — Alissa Prosser
(74) *Attorney, Agent, or Firm* — William D. Hare, Esq.; McNeely, Hare & War, LLP (57) ABSTRACT

The present invention relates to a solid oral pharmaceutical dosage form suitable for making a suspension comprising acid labile benzimidazole compounds and process for preparing the same. The prior art discloses various technical challenges associated with the granules for reconstitution into suspension like agglomeration of particles, viscosity and gelling time. The solid oral pharmaceutical dosage form of the present invention forms a homogeneous suspension upon admixing with an aqueous medium and exhibits desired technical attributes like viscosity, drug release, gelling time, dissolution and reduced adherence to nasogastric and gastric tubes.

20 Claims, 1 Drawing Sheet

PHARMACEUTICAL SUSPENSION DOSAGE FORM OF BENZIMIDAZOLE COMPOUNDS AND PROCESS OF PREPARATION THEREOF

FIELD OF THE INVENTION

The present invention relates to a solid oral pharmaceutical dosage form suitable for making a suspension comprising acid labile benzimidazole compounds and process for preparing the same. The prior art discloses various technical challenges associated with the granules for reconstitution into suspension like agglomeration of particles, viscosity and gelling time. The solid oral pharmaceutical dosage form of the present invention forms a homogeneous suspension upon admixing with an aqueous medium and exhibits desired technical attributes like viscosity, drug release, gelling time, dissolution and reduced adherence to nasogastric and gastric tubes.

BACKGROUND OF THE INVENTION

Benzimidazole compounds such as omeprazole, esomeprazole, lansoprazole, pantoprazole, rabeprazole are proton pump inhibitors. These compounds inhibit gastric acid secretion and are used as therapeutic agents for stomach ulcers, duodenal ulcers and gastroesophageal reflux disorders.

Benzimidazole compounds are highly susceptible to acidic milieu of stomach and thus are difficult to formulate for oral administration. Further, stability of these benzimidazole compounds is reported to be affected by various environmental conditions such as moisture, heat and light.

Esomeprazole is a substituted benzimidazole compound. It is chemically known as bis (5-methoxy-2-[2(S)-[4-methoxy-3,5-dimethyl-2-pryidinyl)methyl]sulfinyl]-1H-benzimidazole-1-yl, having the following structure:

U.S. Pat. No. 4,255,431, assigned to Aktiebolaget Hassle, discloses omeprazole and therapeutically acceptable salts thereof. U.S. Pat. No. 5,877,192, assigned to Astra Aktiebolag, discloses the use of (−) enantiomer of omeprazole (Esomeprazole), or a pharmaceutically acceptable salt thereof, in the treatment of gastric acid related diseases as a means to decrease inter-individual variation in plasma levels compared to Omeprazole.

U.S. Pat. No. 5,731,002, assigned to Astra, discloses a stable, oral pharmaceutical composition comprising a proton pump inhibitor and a gelling agent for the treatment of gastric acid related diseases in animals.

U.S. Pat. No. 5,840,737, assigned to The Curators of the University of Missouri, discloses a method for treating gastric acid disorders by administering a pharmaceutical composition of omeprazole or lansoprazole in a pharmaceutically acceptable carrier consisting essentially of a bicarbonate salt.

Following formulations of esomeprazole magnesium are approved in the U.S. market:

(I) Delayed release capsules (Equivalent to 20 & 40 mg);
(II) Delayed release suspension (Equivalent to 2.5, 5, 10, 20 & 40 mg base/packet); and
(III) Delayed release oral tablets (Equivalent to 20 mg base).

Delayed release granules for oral suspension is marketed in the USA under the brand name Nexium® especially for patients who face difficulty in swallowing tablets or capsules. Delayed release granules for oral suspension comprises two types of granules (a) enteric coated granules comprising glyceryl monostearate, hydroxypropyl cellulose, hypromellose, magnesium stearate, methacrylic acid copolymer type C, polysorbate 80, sugar spheres, talc, and triethyl citrate and (b) inactive granules comprising dextrose, xanthan gum, crospovidone, citric acid, iron oxide, and hydroxypropyl cellulose.

U.S. Patent Publication No. 2015/0079186, assigned to AstraZeneca, discloses esomeprazole magnesium delayed release granules for oral suspension comprising multitude of enteric coated pellets and a suspension modifying granulate. This patent publication highlights various formulation challenges associated with granules for oral suspension formulation after re-constitution like agglomeration of particles, larger storage volumes, limited shelf-life, need for refrigerator storage, dissolution, and high viscosity of the liquid medium which poses difficulty in administration via nasogastric tube. It also discloses that carrageenan could not be used due to lack of suitable viscoelastic properties. This patent publication suggest use of some essential excipients in a specific ratio in order to achieve dosage form with optimal formulation parameters such as use of solid rapidly gelling granulate mixture which contains a rapidly dissolving diluent (such as dextrose), xanthan gum as gelling agent, an acidic pH-regulating agent (such as citric acid), a water soluble binder (such as hydroxypropyl cellulose), optionally a disintegrant (such as crospovidone). A stable viscosity level is achieved when the ratio of binder and gelling agent in granulate is from 1:2 to 1:3 w/w. Thus, development of multiparticulate based solid oral dosage form of esomeprazole magnesium for extemporaneous reconstitution into a homogeneous liquid suspension exhibiting desired viscosity level requires strict control of process variables and processing conditions.

There is a need in pharmaceutical art to design and prepare powder for oral suspension dosage form of Esomeprazole with novel dosage form strategies which can achieve desired technical attributes. The present invention relates to a process for preparing solid oral dosage form of esomeprazole for extemporaneous reconstitution into a homogeneous liquid suspension. Further, solid oral dosage form prepared according to the manufacturing process of the present invention exhibit desired technical attributes such as viscosity, reconstitution time, dissolution and reduced adherence to the nasogastric and gastric tubes that is comparable to commercially marketed formulation of esomeprazole magnesium.

SUMMARY OF THE INVENTION

One embodiment of the present invention relates to a stable, solid oral dosage form suitable for making a suspension comprising a pharmacologically effective amount of benzimidazole compounds, including but not limited to omeprazole, esomeprazole, lansoprazole, pantoprazole, rabeprazole or pharmaceutically acceptable salt, esters, solvates, polymorphs, enantiomers or mixtures thereof.

Another embodiment of the present invention relates to a stable, solid oral dosage form suitable for making a suspension comprising a pharmacologically effective amount of proton pump inhibitor, preferably esomeprazole or its pharmaceutically acceptable salt, esters, solvates, polymorphs, enantiomers or mixtures thereof present in an amount of about 15% to about 80% by weight of the enteric coated pellets.

In yet another embodiment of the invention, the solid oral dosage form suitable for making a suspension comprises from about 1 to about 100 mg of esomeprazole or its pharmaceutically acceptable salts, esters, solvates, polymorphs, enantiomers or mixtures thereof.

Another embodiment of the present invention encompasses a solid oral dosage form suitable for making a suspension comprising from about 15% to about 80% of esomeprazole or its pharmaceutically acceptable salts, esters, solvates, polymorphs, enantiomers or mixtures thereof by weight of the enteric coated pellets and a pharmaceutically acceptable excipient selected from at least one of diluent, binder, disintegrant, surfactant, alkaline agent, glidant, gelling agent, pH-regulating agent, sweeteners, flavoring agents and other pharmaceutical excipients. Combination of excipients performing the same function may also be used to achieve the desired formulation characteristics.

In yet another embodiment of the invention, the solid oral dosage form suitable for making a suspension comprises (a) first population comprising benzimidazole compound or its pharmaceutically acceptable salts, esters, solvates, polymorphs, enantiomers, or mixtures thereof and (b) second population comprising inactive granulate or powder or both.

In yet another embodiment of the invention, the solid oral dosage form suitable for making a suspension comprises (a) first population comprising enteric coated pellets of esomeprazole or its pharmaceutically acceptable salts, esters, solvates, polymorphs, enantiomers, or mixtures thereof and (b) second population comprising inactive granulate or powder or both.

In another embodiment of the invention, the solid oral dosage form suitable for making a suspension comprises (a) enteric coated pellets of esomeprazole or its pharmaceutically acceptable salts, esters, solvates, polymorphs, enantiomers or mixtures thereof and (b) suspension modifying inactive granulate.

In yet another embodiment of the invention, the solid oral dosage form suitable for making a suspension comprises (a) enteric coated pellets of esomeprazole or its pharmaceutically acceptable salts, esters, solvates, polymorphs, enantiomers or mixtures thereof and (b) suspension modifying inactive granulate, wherein the granulate comprises mannitol and/or lactose as the diluent.

In yet another embodiment of the invention, the solid oral dosage form suitable for making a suspension comprises (a) enteric coated pellets of esomeprazole or its pharmaceutically acceptable salts, esters, solvates, polymorphs, enantiomers or mixtures thereof and (b) suspension modifying inactive granulate, wherein the granulate comprises a gelling agent.

In yet another embodiment of the invention, the solid oral dosage form suitable for making a suspension comprises (a) enteric coated pellets of esomeprazole or its pharmaceutically acceptable salts, esters, solvates, polymorphs, enantiomers, or mixtures thereof and (b) suspension modifying inactive granulate; wherein the ratio of binder to gelling agent in the suspension modifying inactive granulate is less than 1:2.

In yet another embodiment of the invention, the solid oral dosage form suitable for making a suspension comprises (a) enteric coated pellets of esomeprazole or its pharmaceutically acceptable salts, esters, solvates, polymorphs, enantiomers, or mixtures thereof and (b) suspension modifying inactive granulate; wherein the ratio of binder to gelling agent in the suspension modifying inactive granulate is granulate is more than 1:3.

In yet another embodiment of the invention, the solid oral dosage form suitable for making a suspension comprises (a) enteric coated pellets of esomeprazole or its pharmaceutically acceptable salts, esters, solvates, polymorphs, enantiomers or mixtures thereof and (b) suspension modifying inactive granulate, wherein the granulate is substantially free of binder.

In yet another embodiment of the invention, the solid oral dosage form suitable for making a suspension comprises (a) enteric coated pellets of esomeprazole or its pharmaceutically acceptable salts, esters, solvates, polymorphs, enantiomers or mixtures thereof and (b) suspension modifying inactive granulate, wherein the granulate comprises a binder. The binder (if present) can be water-insoluble binder, water-soluble binder, or a mixture of water-soluble and water-insoluble binder.

In yet another embodiment of the invention, the solid oral dosage form suitable for making a suspension comprises (a) enteric coated pellets of esomeprazole or its pharmaceutically acceptable salts, esters, solvates, polymorphs, enantiomers or mixtures thereof and (b) suspension modifying inactive granulate, wherein the granulate comprises xanthan gum as the gelling agent.

In yet another embodiment of the invention, the solid oral dosage form suitable for making a suspension comprises (a) enteric coated pellets of esomeprazole or its pharmaceutically acceptable salts, esters, solvates, polymorphs, enantiomers or mixtures thereof and (b) suspension modifying inactive granulate, wherein the granulate is free of xanthan gum.

In yet another embodiment of the invention, the solid oral dosage suitable for making a suspension form comprises (a) enteric coated pellets of esomeprazole or its pharmaceutically acceptable salts, esters, solvates, polymorphs, enantiomers or mixtures thereof and (b) suspension modifying inactive granulate, wherein the granulate comprises carrageenan as the gelling agent.

In yet another embodiment of the invention, the solid oral dosage form suitable for making a suspension comprises (a) enteric coated pellets of esomeprazole or its pharmaceutically acceptable salts, esters, solvates, polymorphs, enantiomers or mixtures thereof and (b) suspension modifying inactive granulate, wherein the granulate comprises a mixture of carboxymethyl cellulose and microcrystalline cellulose as the gelling agent.

In yet another embodiment of the invention, the solid oral dosage form suitable for making a suspension comprises (a) enteric coated pellets of esomeprazole or its pharmaceutically acceptable salts, esters, solvates, polymorphs, enantiomers or mixtures thereof and (b) suspension modifying inactive granulate, wherein the granulate optionally comprises bicarbonate and/or carbonate salts.

In yet another embodiment of the invention, the solid oral dosage form suitable for making a suspension comprises (a) enteric coated pellets of esomeprazole or its pharmaceutically acceptable salts, esters, solvates, polymorphs, enantiomers or mixtures thereof and (b) suspension modifying inactive granulate, wherein the composition provides comparable gelling time, pH, viscosity, viscoelastic properties and dissolution to Nexium® delayed release granules.

In yet another embodiment of the invention, the solid oral dosage form suitable for making a suspension comprises (a)

enteric coated pellets of esomeprazole or its pharmaceutically acceptable salts, esters, solvates, polymorphs, enantiomers or mixtures thereof and (b) suspension modifying inactive granulate, wherein the composition provides comparable dissolution to Nexium® delayed release granules.

In another embodiment, solid oral dosage form suitable for making a suspension comprising esomeprazole or pharmaceutically acceptable salts, esters, solvates, polymorphs, enantiomers or mixtures thereof of the present invention includes particle size of esomeprazole or its pharmaceutically acceptable salts, esters, solvates, polymorphs, enantiomers or mixtures thereof of, wherein $D_{90}$ is less than about 100 µm.

In yet another embodiment of the present invention, there is provided a process for preparing solid oral dosage form suitable for making a suspension comprising esomeprazole or its pharmaceutically acceptable salts, esters, solvates, polymorphs enteric coated pellets, wherein the process comprises a) coating the inert core with aqueous dispersion or suspension of esomeprazole or its pharmaceutically acceptable salts, esters, solvates, polymorphs and optionally other pharmaceutical excipients to form a drug layer, b) applying the sub-coating layer on the drug layer followed by optionally repeating the step of applying the sub-coating layer and c) subsequently coating the sub-coating layer with one or more enteric layers using an aqueous dispersion of at least one enteric polymer and d) drying the enteric coated esomeprazole or its pharmaceutically acceptable salts, esters, solvates, polymorphs pellets. In another embodiment, an intermediate coating is applied on the drug layer before the sub-coating layer.

In yet another embodiment of the present invention, esomeprazole or its pharmaceutically acceptable salts, esters, solvates, polymorphs can be present inside the pellets prepared by process such as wet granulation, dry granulation, dry blending, and extrusion and spheronization.

The suspension modifying inactive granulate comprises a diluent, a gelling agent, optionally binder, optionally an acidic pH-regulating agent, and optionally a disintegrant. In one embodiment, the diluent is rapidly dissolving in suspending aqueous medium.

In another embodiment of the present invention, the suspension modifying inactive granulate of the solid oral dosage form suitable for making a suspension of the invention is prepared by wet or dry process. The wet and dry processes include, but are not limited to, wet granulation, dry granulation, dry blending, extrusion and spheronization. Other formulation techniques are also contemplated within the scope of the present invention.

In another embodiment, the suspension modifying inactive granulate is prepared by a process in which the diluent and the gelling agent are mixed and granulated together, and then dried.

In another embodiment, the suspension modifying inactive granulate is prepared by a process comprising the following steps:
(i) mixing the diluent, gelling agent, optionally pH-regulating agent, and optionally disintegrant;
(ii) optionally preparing a binder solution;
(iii) granulating the mixture of step (i) with an organic solvent or the solution of step (ii); and
(iv) drying the granulates of step (iii);
(v) grinding or milling the granulates of step (iv) to obtain the suspension modifying inactive granulate.

In another embodiment of the present invention, the enteric coated esomeprazole or its pharmaceutically acceptable salts, esters, solvates, polymorphs pellets are mixed with suspension modifying inactive granulate to form the solid oral dosage form.

In another embodiment of the present invention, the enteric coated esomeprazole or its pharmaceutically acceptable salts, esters, solvates, polymorphs pellets are mixed with a pharmaceutically acceptable excipient to form the solid oral dosage form selected from at least one of diluent, binder, disintegrant, surfactant, alkaline agent, glidant, gelling agent, pH-regulating agent, sweeteners, flavoring agents, and the like.

In another embodiment of the present invention, the solid oral dosage form suitable for making a suspension comprising esomeprazole or pharmaceutically acceptable salts, esters, solvates, polymorphs, enantiomers or mixtures thereof has a desirable bulk density.

In yet another embodiment of the present invention, the solid oral dosage suitable for making a suspension form comprising esomeprazole or pharmaceutically acceptable salts, esters, solvates, polymorphs, enantiomers or mixtures thereof has a desirable tapped density.

In another embodiment of the present invention, the enteric coated pellets present in the pharmaceutical composition comprising esomeprazole or its pharmaceutically acceptable salts, esters, solvates, polymorphs, enantiomers or mixtures thereof have an average diameter of about 0.1 to 3 mm. Particularly, the diameter is between 0.2-2 mm.

In another embodiment, the solid oral dosage form comprising esomeprazole or its pharmaceutically acceptable salts, esters, solvates, polymorphs, enantiomers or mixtures thereof of the present invention exhibits a biphasic dissolution profile whereby negligible drug release is observed in acid stage (such as 0.1N HCL) and substantial drug release is expected to be observed at buffer stage pH 6.8 (such as phosphate buffer pH 6.8). Particularly, the solid oral dosage form exhibits a dissolution profile comparable to the Nexium® delayed release granules for suspension wherein 0-5% drug is released in 0.1N HCl (300 ml) for 2 hours and at least 80% drug is released in phosphate buffer (pH 6.8; 1000 ml) using a USP II apparatus at 100 rpm for 30 minutes.

In further embodiment, the present invention includes method of using the solid oral dosage form comprising spheronized granules of esomeprazole or pharmaceutically acceptable salts, esters, solvates, polymorphs, enantiomers or mixtures thereof in the treatment of gastroesophageal reflux disease (GERD), risk reduction of non-steroidal anti-inflammatory drug (NSAID) associated gastric ulcer, H. pylori eradication to reduce the risk of duodenal ulcer recurrence and pathological hypersecretory conditions including Zollinger-Ellison syndrome. The solid oral dosage form suitable for making a suspension of present invention may also include a wide range of dosage levels and additional agents such as sweeteners, taste masking/improving agents and tonicity agents.

In yet another embodiment of the invention, the present invention provides a re-constituted suspension comprising:
(i) a solid oral dosage form comprising a (a) first population comprising enteric coated pellets of esomeprazole or its pharmaceutically acceptable salts, esters, solvates, polymorphs, enantiomers or mixtures thereof and (b) a second population comprising inactive granulate/powder; and
(ii) an aqueous medium.
Particularly, the aqueous medium is water.

In yet another embodiment of the invention, the present invention provides a re-constituted suspension comprising:
(i) solid oral dosage form comprising (a) enteric coated pellets of esomeprazole or its pharmaceutically acceptable salts, esters, solvates, polymorphs, enantiomers or mixtures thereof and (b) suspension modifying inactive granulate; and (ii) an aqueous medium.

Particularly, the aqueous medium is water.

In yet another embodiment of the invention, the viscosity and gelling time of the formed suspension is sufficient to prevent sedimentation or segregation of pellets suspended therein.

DETAILED DESCRIPTION OF THE INVENTION

The present invention can be more readily understood by reading the following detailed description of the invention and study of the included examples.

As used herein, the term "dosage form", as in pharmaceutical dosage form, is intended to encompass a drug product comprising benzimidazole compounds such as esomeprazole, rabeprazole or its pharmaceutically acceptable salts, esters, solvates, polymorphs, stereoisomers or mixtures thereof, and other inert ingredient(s) (pharmaceutically acceptable excipients). Such pharmaceutical dosage forms are synonymous with "formulation" and "composition". Dosage form of the invention include, but are not limited to, granules, mini tablets, capsules (hard and soft gelatin capsules), powders, microcapsules and the like. Preferably, the dosage form refers to granules for oral suspension. More preferably, the dosage form refers to delayed release granules for oral suspension.

The term "acid labile benzimidazole" as used herein refers to benzimidazole compounds of therapeutic interest whose half-life is less than 10 minutes in an aqueous solution that has a pH less than 4, for example, esomeprazole, pantoprazole, lansoprazole, rabeprazole and the like.

The term "delayed release" as used herein, refers to a solid dosage, which releases a drug at a time other than promptly after administration. For the purpose of this invention enteric-coated pellets are delayed release dosage forms.

"Esomeprazole" and "Rabeprazole" as used herein, refers to the free acid form, its salts, esters, solvates, polymorphs, enantiomers or mixtures thereof. Preferably, the salt of esomeprazole is esomeprazole magnesium. Preferably, the salt of rabeprazole is rabeprazole sodium.

The term "excipient" means a pharmacologically inactive component such as a diluent, binder, disintegrant, alkaline agent, surfactant, glidants, gelling agent, pH-regulating agent, sweeteners, flavoring agents, carrier, or the like. The excipients that are useful in preparing the solid oral pharmaceutical dosage form are generally safe, non-toxic and are acceptable for veterinary as well as human pharmaceutical use. Reference to an excipient includes both one and more than one such excipient. Co-processed excipients are also covered under the scope of present invention. Further, excipient may be in the form of powders or in the form of dispersion. Combination of excipients performing the same function may also be used to achieve the desired formulation characteristics.

Unless otherwise stated the weight percentages expressed herein are based on the final weight of the composition or formulation.

"Substantially free of binder" as used herein, refers to the solid oral dosage form of esomeprazole or its pharmaceutically acceptable salts, esters, solvates, polymorphs, enantiomers or mixtures thereof, which contains less than 2% binder by weight of the inactive granulate. More particularly, it refers to the solid oral dosage form of esomeprazole or its pharmaceutically acceptable salts, esters, solvates, polymorphs, enantiomers or mixtures thereof which does not contain a binder.

As used herein, the term "about" means ±approximately 20% of the indicated value, such that "about 10 percent" indicates approximately 08 to 12%.

As used herein, the term "stable" means refers to chemical stability, wherein not more than 5% w/w of total related substances are formed on storage at 40° C. and 75% relative humidity (R.H.) or at 25° C. and 60% R.H. for a period of at least three months.

"Bulk density" as used herein, refers to the ratio of the mass of an untapped powder sample and its volume including the contribution of the interparticulate void volume. Bulk density indicates mass of a powder material that can be filled in per unit volume.

"Tapped density" as used herein, refers to the ratio of the mass of a tapped powder sample and its volume. Tapped density of granules can be determined by using a suitable apparatus such as Electrolab tap density tester.

In another embodiment the solid oral dosage form of the present invention includes particle size of esomeprazole or its pharmaceutically acceptable salts, esters, solvates, polymorphs, enantiomers or mixtures thereof, wherein $D_{90}$ is less than about 100 μm.

The present invention relates to solid oral dosage form suitable for making a suspension of esomeprazole or its pharmaceutically acceptable salts, esters, solvates, polymorphs, enantiomers or mixtures thereof such that the composition exhibits desired technical attributes such as viscosity, reconstitution time, dissolution which is comparable to the commercially available Nexium® delayed release granules for oral suspension. Preferably, salt of esomeprazole is esomeprazole magnesium.

One embodiment of the invention encompasses a solid oral dosage form suitable for making a suspension comprising esomeprazole or a salt thereof and a pharmaceutically acceptable excipient selected from at least one of diluent, binder, disintegrant, surfactant, alkaline agent, glidant, gelling agent, pH-regulating agent, sweeteners, flavoring agents and other pharmaceutical excipients.

Active Enteric Coated Pellets:

The present invention provides stable solid oral pharmaceutical dosage form comprising multiplicity of enteric-coated pellets. The enteric-coated pellets comprise a) core comprising benzimidazole compound in or on the core as a drug layer, b) at least one sub-coating layer, and c) at least one enteric layer. An intermediate layer can also be applied on the drug layer before the sub-coating layer.

According to the invention, the inert core can be water-soluble, water-swellable and water-insoluble. Non-pareil seeds (NPS) or sugar spheres exemplify an inert core of water-soluble type. NPS are white, spherical particles of 62-92% sucrose and rest starch. NPS are commercially available from JRS Pharma, USA in various sieve sizes. Suitable examples of water swellable cores are microcrystalline cellulose spheres, commercially available from FMC Corporation under the trade name CELPHERE®. Exemplary water insoluble inert cores are glass beads and coarse grade silicon beads. The inert core must be of sufficient density and strength to withstand stress and strain of coating process. Preferably, the inert core unit is made up of inert non-pareil sugar spheres or microcrystalline cellulose.

The drug layer comprises esomeprazole or its pharmaceutically acceptable salts, binder, disintegrants and other pharmaceutical acceptable excipients like anti-tacking agents, solvents for dissolving the binders and/or the esomeprazole or its pharmaceutically acceptable salts, surfactants. The inert core is coated with a dispersion of esomeprazole or its pharmaceutically acceptable salts, binder, and disintegrants.

The drug layer is applied to the inert core by any conventional techniques known in the art. An organic or aqueous solvent may be used during drug layering process. Sub-coating provides physical separation between the active part of the core which comprises the drug and the enteric coating. The solid oral pharmaceutical dosage form of the present invention may comprise one or more sub-coating layers. The composition of these sub-coating layers may be similar or different. Various materials used for sub-coating layer include, but are not limited to sugar, polyvinyl alcohol, polyvinylpyrrolidone, polyethylene glycol, polyvinyl acetate, methylcellulose, hydroxypropylmethyl cellulose, hydroxypropyl cellulose, ethylcellulose, or mixtures thereof. Various materials used for intermediate layer comprises of basic metal compounds, icing sugar, starch, or mixtures thereof.

The solid oral pharmaceutical dosage form suitable for making a suspension of the present invention one or more enteric layers, of same or different enteric polymers, disposed on the sub-coated beads. The enteric layer consists essentially of enteric polymers. Besides, enteric layer may also contain plasticizers, opacifying agents, anti-tacking agents, stabilizers, antifoaming agents, surfactants, antistatic agent, colorants, and pigments to enhance the processability, functionality and elegance of the said layers.

Diluents or fillers are substances which usually provide bulk to the composition. Various useful fillers or diluents include, but are not limited to calcium carbonate, calcium phosphate, dibasic anhydrous, calcium phosphate, dibasic dihydrate, calcium phosphate tribasic, calcium sulphate, cellulose powdered, silicified microcrystailine cellulose, cellulose acetate, lactitol, lactose, mannitol, magnesium carbonate, magnesium oxide, maltodextrin, mannitol, microcrystalline cellulose, polydextrose, simethicone, sodium alginate, sodium chloride, sorbitol, starch, pregelatinized starch, and xylitol, or mixtures thereof. The diluent may constitutes from about 10 to about 95% by weight of enteric coated pellets and/or suspension modifying inactive granulate. In particular, the diluents for suspension modifying inactive granulate are lactose and/or mannitol.

Binders impart cohesiveness to formulation. Various useful binders include, but are not limited to hydroxypropylmethyl cellulose, hydroxypropyl cellulose, acacia, alginic acid, carbomer, carboxymethylcellulose sodium, ceratonia, dextrin, dextrose, gelatin, guar gum, hydroxyethyl cellulose, hydroxyethyhnethyl cellulose, magnesium aluminium silicate, maltodextrin, maltose, methylcellulose, polydextrose, polyethylene oxide, polymethacrylates, povidone, sodium alginate, starch, pregelatinized starch, stearic acid, sucrose and zein, or mixtures thereof.

Examples of water insoluble binders includes cellulose derivatives (e.g. ethylcellulose), polyvinyl acetate (Kollicoat SR30D), phthalate based polymers and copolymers, neutral copolymers based on ethyl acrylate and methylmethacrylate, copolymers of acrylic and methacrylic acid esters, and with quaternary ammonium groups, such as Eudragit NE, Eudragit RS, Eudragit RS30D, Eudragit RL and Eudragit RL30D, or mixtures thereof. Water swellable binders may also be used to achieve the pharmaceutical compositions of the present invention. The binders may constitutes from about 0% to about 20% by weight of enteric coated pellets and/or suspension modifying inactive granulate.

Various useful disintegrants include, but are not limited to, alginic acid, calcium phosphate, tribasic, carboxymethylcellulose calcium, carboxymethylcellulose sodium, colloidal silicon dioxide, croscarmellose sodium, crospovidone, docusate sodium, guar gum, low substituted hydroxypropyl cellulose, magnesium aluminun silicate, methylcellulose, microcrystalline cellulose, povidone, sodium alginate, sodium starch glycolate, polacrilin potassium, silicified microcrystalline cellulose, starch or pre-gelatinized starch, or mixtures thereof. Disintegrants constitute from about 0% to about 20% by weight of enteric coated pellets and/or suspension modifying inactive granulate.

Glidants improve flowability and accuracy of dosing. Glidants used in the composition include, but are not limited to, tribasic calcium phosphate, calcium silicate, cellulose, powdered, colloidal silicon dioxide, magnesium silicate, magnesium trisilicate, starch and talc or mixtures thereof.

Surfactants or surface-active agents improve wettability of the dosage form and/or enhance its dissolution. Surfactants contemplated in the present invention include but are not limited to anionic surfactants, amphoteric surfactants, non-ionic surfactants and macromolecular surfactants. Suitable examples of anionic surfactants include but are not limited to sodium lauryl sulphate, sodium cetyl stearyl sulphate or sodium dioctyl sulphosuccinate etc. Suitable example of an amphoteric surfactant include but is not limited to lecithin. Suitable examples of non-ionic surfactants include but is not limited to cetyl alcohol, stearyl alcohol, cetyl stearyl alcohol, cholesterol, sorbitan fatty acid esters such as sorbitan mono-oleate, polyoxyethylene sorbitan fatty acid esters such as polysorbate 20, polyoxyethylene fatty acid glycerides such as macrogol 1000 glycerol monostearate, polyoxyethylene fatty acid esters such as polyoxyl 40 stearate, polyoxyethylene fatty alcohol ethers such as polyoxyl 10 oleyl ether, glycerol fatty acid esters such as glycerol monostearate, commercially available SEPITRAP® 80 or SEPITRAP® 4000 etc. Surfactant may constitute from about 0% to about 5% by weight of enteric coated pellets and/or suspension modifying inactive granulate.

Alkaline agent may be used to provide a microenvironment of pH above 7 around the acid labile benzimidazole derivative. Suitable alkaline agents include, but are not limited to, pharmacologically tolerated alkali metal, alkaline earth metal or metal salts of weak acids such as sodium carbonate which can be anhydrous or hydrous, calcium carbonate and magnesium carbonate and the pharmacologically tolerated hydroxides and oxides of alkaline earth and earth metals such as magnesium hydroxide and magnesium oxide.

Suitable solvents include aqueous or organic solvents. Preferable solvents include, but are not limited to, water, esters such as ethyl acetate; ketones such as acetone; alcohols such as methanol, ethanol, isopropanol, butanol or hydro-alcoholic solvent; dichloromethane, chloroform, dimethyl acetamide (DMA), dimethyl sulfoxide (DMSO), ether, diethyl ether and combinations thereof.

The gelling time is the time required before substantially all of the enteric coated pellets in the prepared suspension remain suspended in the liquid medium and not sink to the bottom of the vessel (such as beaker) used for its preparation. The gelling time is in general shorter than 5 minutes, particularly less than 4 minutes, more particularly less than 3 minutes, and much particularly less than 2 minutes.

Various useful gelling agents include, but are not limited to, co-processed spray dried forms of microcrystalline cellulose and carboxymethyl cellulose such as those marketed under the trade names Avicel® RC-501, Avicel® RC-581, Avicel® RC-591, and Avicel® CL-611, carrageenan, carboxymethylcellulose sodium, xanthan gum, guar gum, locust bean gum, tragacanth, modified cellulose derivatives, acacia, agar, alginic acid, sodium carboxymethyl cellulose, fucoidan, furcellaran, laminaran or similar gel forming agents. Gelling agents may constitute from about 0.05% to about 20% by weight of enteric coated pellets and/or suspension modifying inactive granulate.

Various useful pH-regulating agent include, but are not limited to, citric acid, tartaric acid, succinic acid, malic acid, lactic acid, benzoic acid, sorbic acid and ascorbic acid and other substances. The pH of the suspension granules when suspended in a medium such as water is in the range of between 3.0 and 6.0, particularly in the range of 3.5 and 5.5, and more particularly in the range of 4.0 and 5.0.

The polymers useful in the enteric layer include, but not limited to, cellulose acetate phthalate, cellulose acetate trimellitate, hydroxypropylmethylcellulose acetate succinate (HPMCAS), hydroxypropyl methylcellulose phthalate (HPMCP), shellac, polyvinylacetate phthalate, acrylic acid polymers & copolymers, and methacrylic acid polymers & copolymers, zein or any combinations thereof. The enteric polymers may constitute from about 2% to about 50% by weight of enteric-coated beads. In particular, enteric polymer is acrylic acid polymer and copolymer. More particularly, it is methacrylic acid polymer and copolymer.

In another embodiment, the solid oral pharmaceutical dosage form comprises from about 15% to about 80% by weight of esomeprazole or its pharmaceutically acceptable salts, esters, solvates, polymorphs, enantiomers or mixtures thereof and a pharmaceutically acceptable excipient selected from at least one of diluent, binder, disintegrant, surfactant, alkaline agent, glidant, gelling agent, pH-regulating agent, sweeteners, flavoring agents and other pharmaceutical excipients.

In yet another embodiment of the invention, the solid oral pharmaceutical compositions comprise from about 1 mg to about 100 mg of esomeprazole. Preferably, the pharmaceutical compositions comprise about 1 mg to about 40 mg of esomeprazole. Particularly, esomeprazole magnesium salt is used.

In yet another embodiment of the invention, the solid oral dosage form comprises (a) enteric coated pellets and (b) suspension modifying inactive granulate, wherein the enteric coated pellets comprising from about 15% to about 80% esomeprazole or its pharmaceutically acceptable salts, esters, solvates, polymorphs, enantiomers or mixtures thereof by weight of the enteric coated pellets and a pharmaceutically acceptable excipient selected from at least one of diluent, binder, disintegrant, surfactant, alkaline agent, glidant, gelling agent, pH-regulating agent, sweeteners, flavoring agents and other pharmaceutical excipients.

In another embodiment of the invention, the solid oral pharmaceutical dosage form is a granule. More particularly, the solid oral pharmaceutical dosage form is delayed release granules for oral suspension.

The solid oral dosage form suitable for making a suspension of the present invention can be subjected to in-vitro dissolution evaluation according to Test 711 "Dissolution" in the United States Pharmacopoeia 37, United States Pharmacopoeial Convention, Inc., Rockville, Md., 2014 ("USP") to determine the rate at which the active substance is released from the dosage form. When comparing the test and reference products, dissolution profiles should be compared using a similarity factor ($f_2$). The similarity factor is a logarithmic reciprocal square root transformation of the sum of squared error and is a measurement of the similarity in the percent (%) of dissolution between the two curves.

$$f_2 = 50 \cdot \log\{[1+(1/n)\Sigma_{t=1}^{n}(R_t-T_t)^2]^{-0.5} \cdot 100\}$$

Two dissolution profiles are considered similar when the $f_2$ value is equal to or greater than 50.

In another embodiment, the solid oral dosage form of the present invention exhibited biphasic drug release whereby negligible drug is released in 300 mL of 0.1N hydrochloric acid, sampling at 120 minutes and substantial drug is released in 1000 mL of sodium phosphate buffer (pH 6.8) sampling at 10, 20, 30, 45 and 60 minutes (Office of Generic Drugs dissolution database) using a USP II apparatus (paddle) at a temperature of 37±0.5° C. and a rotation speed of 100 revolutions per minute. Particularly, the solid oral dosage form exhibits a dissolution profile comparable to the Nexium® delayed release granules for suspension wherein 0-5% drug is released in 0.1N HCl (300 ml) for 2 hours and at least 80% drug is released in phosphate buffer (pH 6.8; 1000 ml) using a USP II apparatus at 100 rpm for 30 minutes.

The solid dosage form comprising the enteric coated pellets and inactive granulates/powder/suspension modifying inactive granulate are packed in a suitable package such as sachet, foil or pouch which can be unit dose or multi dose. In particular, the package is a unit dose package.

Prior to use, the solid dosage form of the sachet is emptied into a predefined volume of an aqueous medium and stirred. This forms a suspension which is suitable for administration. Having described the invention with reference to certain preferred embodiments, other embodiments will become apparent to one skilled in the art from consideration of the specification. The invention is further defined by reference to the following examples describing in detail method for the preparation and testing of esomeprazole magnesium pharmaceutical dosage form. It will be apparent to those skilled in the art that many modifications, both to materials and methods, may be practiced without departing from the scope of the invention. Following examples are set out to illustrate the invention and do not limit the scope of the present invention.

EXAMPLES

Example 1

Enteric coated pellets comprising benzimidazole compounds such as esomeprazole magnesium or rabeprazole sodium can be prepared by any of the methods disclosed in the prior arts such as disclosed in U.S. Patent Publication No. 2011/0177164 assigned to Jubilant Life Sciences Ltd., U.S. Pat. No. 8,865,212 assigned to Jubilant Generics and U.S. Pat. Nos. 5,714,504, 6,428,810 and 6,090,827 assigned to AstraZeneca Ab.

Example 2

Delayed Release Coated Pellets of Esomeprazole as Given in Table 1

| Ingredients | % w/w |
|---|---|
| Drug Layering | |
| Sugar sphere | 18.78 |
| Esomeprazole magnesium | 25.11 |
| Hydroxypropylmethyl cellulose | 1.70 |
| Polysorbate 80 | 0.50 |
| Purified water | q.s. |
| Sub Coating | |
| Hydroxypropyl cellulose | 9.03 |
| Magnesium stearate | 1.23 |
| Talc | 17.08 |
| Purified water | q.s. |
| Delayed Release Coating | |
| Methacrylic acid copolymer | 23.74 |
| Glycerol monostearate | 1.23 |
| Polysorbate 80 | 0.13 |
| Triethyl citrate | 1.47 |
| Purified water | q.s. |

Procedure:

1. Hydroxypropylmethyl cellulose and polysorbate 80 was mixed with purified water.
2. Esomeprazole magnesium was added to the mixture of step 1 and mixed.
3. The mixture of step 2 was coated on sugar spheres to form drug layered pellets.
4. Hydroxypropyl cellulose was added in a portion of purified water and stirred.
5. Talc and magnesium stearate were added to remaining portion of purified water and homogenized and added to mixture of step 4 and mixed.
6. The drug layered pellets of step 3 were coated with the mixture of step 5 to form seal/sub-coated pellets.
7. Glyceryl monostearate was added to purified water heated to 60° C. and mixed.
8. Polysorbate 80 and triethyl citrate was added to the mixture of step 7 and stirred till the temperature came down to room temperature.
9. Methacrylic acid copolymer was passed through a suitable mesh.
10. Mixture of step 8 was added to step 9.
11. Seal coated pellets of step 6 were coated with the mixture of step 10 to form delayed release pellets.

Examples 3-6

Solid Oral Dosage Form of Esomeprazole as Given in Table 2

TABLE 2

| Composition | Example 3 | Example 4 | Example 5 | Example 6 |
|---|---|---|---|---|
| | Weight (in mg) | | | |
| Delayed release pellets of esomeprazole magnesium equivalent to 40 mg esomeprazole as per example 2 | | | | |
| Suspension modifying inactive granulate | | | | |
| Ratio of Hydroxypropyl cellulose:xanthan gum | 0:75 | 1:5 | 1:7.5 | 1:16 |
| Dextrose | 2846.00 | 2831.00 | 2836.00 | 2836.00 |
| Xanthan gum | 75.00 | 75.00 | 75.00 | 80.00 |
| Crospovidone | 75.00 | 75.00 | 75.00 | 75.00 |
| Citric acid | 2.50 | 2.50 | 2.50 | 2.50 |
| Iron oxide | 1.50 | 1.50 | 1.50 | 1.50 |
| Hydroxypropyl cellulose | 0.00 | 15.00 | 10.00 | 5.00 |
| Hydro alcoholic Solvent | q.s. | q.s. | q.s. | q.s. |

Procedure:

1. Dextrose, xanthan gum, crospovidone, citric acid, iron oxide, hydroxypropyl cellulose were passed through suitable mesh and mixed together.
2. The mixture of step 1 was granulated with hydro alcoholic solvent.
3. The granulated mixture of step 2 was dried.
4. Dried granulated mixture of step 3 and Delayed Release pellets (example 2) were mixed and packed in a sachet.

TABLE 3

Drug Release of Esomeprazole in 0.1N HCl (300 mL) for 2 hours followed by addition of sodium phosphate buffer pH 6.8 (1000 mL) in USP Apparatus II (Paddle) at 100 rpm for 60 minutes

| Time Point (minutes) | Nexium ® delayed release granules | Example 3 | Example 4 | Example 5 | Example 6 |
|---|---|---|---|---|---|
| 120 (0.1N HCl) | 0 | 0 | 0 | 0 | 0 |
| 10 | 47 | 49 | 38 | 53 | 27 |
| 20 | 96 | 96 | 89 | 97 | 74 |
| 30 | 93 | 95 | 95 | 98 | 94 |
| 45 | 91 | 94 | 94 | 95 | 97 |
| 60 | 89 | 92 | 93 | 94 | 96 |

Example 7-11

Solid Oral Dosage Form of Esomeprazole as Given in Table 4

TABLE 4

| Composition | Example 7 | Example 8 | Example 9 | Example 10 | Example 11 |
|---|---|---|---|---|---|
| | Weight (in mg) | | | | |
| Delayed release pellets of esomeprazole magnesium equivalent to 40 mg esomeprazole as per example 2 | | | | | |
| Suspension modifying inactive granulate | | | | | |
| Lactose/Mannitol/Dextrose | 3000.00 | 3000.00 | 2900.00 | 3000.00 | 2800.00 |
| Carrageenan | 75.00 | — | 75.00 | 80.00 | — |
| Mixture of carboxymethyl cellulose and microcrystalline cellulose | — | 75.00 | — | — | 80 |
| Crospovidone | 75.00 | 75.00 | 75.00 | 75.00 | 75.00 |
| Citric acid | 2.50 | 2.50 | 2.50 | 2.50 | 2.50 |
| Iron oxide | 1.50 | 1.50 | 1.50 | 1.50 | 1.50 |
| Hydroxypropyl cellulose | 0.00 | 15.00 | 10.00 | — | — |
| Hydroxypropylmethyl cellulose | — | — | — | 5.00 | 5.00 |
| Solvent | q.s. | q.s. | q.s. | q.s. | q.s. |

Same procedure can be used as for Examples 3-6.

Example 12

Figure 1:
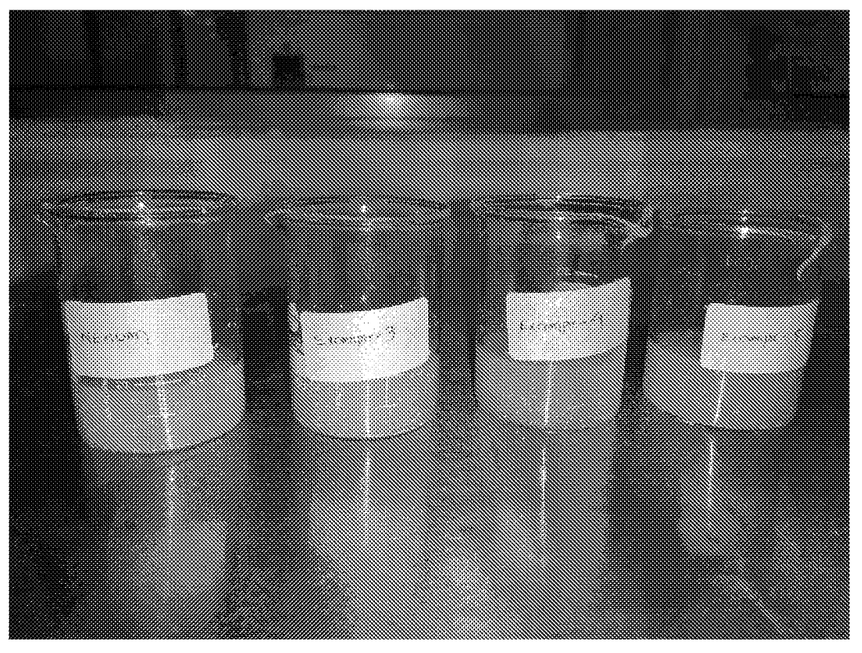
FIG. 1. Showing suspensions formed after mixing the solid oral dosage forms of the present invention (Examples 3-5) and Nexium® delayed release granules with water.

Gelling Time of Solid Oral Dosage Form of Esomeprazole and Nexium® Granules for Suspension Equivalent to 40 mg Esomeprazole The solid oral dosage form of esomeprazole of present invention for suspension and Nexium® granules for suspension equivalent to 40 mg esomeprazole were added respectively to beakers containing 15 mL of water. The samples were stirred for 15 seconds and allowed to rest until 55 seconds from start, after which it was again stirred for 5 seconds and the samples were inspected for 30 seconds. If the pellets were not distributed in the liquid medium but assembled at the bottom of the beaker, the process was repeated, i.e. waiting 25 seconds further and stirring 5 seconds, then waiting for 2 minutes, followed by inspecting for 30 seconds, until substantially all of the pellets remained distributed in the liquid medium. The time needed for the pellets to remain in suspension in the liquid medium was recorded (Table 5). FIG. 1 shows the suspensions formed after mixing the solid oral dosage forms of the present invention (Examples 3-5) and Nexium® delayed release granules with water as per the above mentioned procedure.

TABLE 5

| Sample | Gelling time (minutes) |
|---|---|
| Example 3 | 2-3 |
| Example 4 | 2-3 |
| Example 5 | 2-3 |
| Example 6 | 2-3 |
| Nexium ® delayed release granules for suspension (equivalent to 40 mg esomeprazole) | 2-3 |

The suspensions prepared from the solid oral dosage form showed comparable gelling time, viscosity and dissolution with respect to the marketed Nexium delayed release granules for oral suspension.

We claim:

1. A solid oral dosage form consisting of enteric coated pellets of esomeprazole magnesium and a suspension modifying inactive granulate, wherein:
    the enteric coated pellets of esomeprazole magnesium consist of:
    18.78% (w/w) of sugar spheres;
    a first layer on the spheres and consisting of 25.11% (w/w) esomeprazole magnesium, 1.7% (w/w) hydroxypropylmethyl cellulose and 0.5% (w/w) polysorbate 80;
    a second layer on the spheres positioned over the first layer and consisting of 9.03% (w/w) hydroxypropyl cellulose, 1.23% (w/w) magnesium stearate and 17.08% (w/w) talc; and
    a third layer on the spheres positioned over the second layer and consisting of 23.74% (w/w) methacrylic acid copolymer, 1.23% (w/w) glycerol monostearate, 0.13% (w/w) polysorbate 80 and 1.47% (w/w) triethyl citrate over the second layer, wherein the weight percentages are of the enteric coated pellets; and
    the suspension modifying inactive granulate consists of 95.11% (w/w) of lactose/mannitol/dextrose, 2.38% (w/w) of carrageenan, 2.38% (w/w) of crospovidone, 0.08% (w/w) of citric acid and 0.05% (w/w) of iron oxide.

2. The solid oral dosage form of claim 1, wherein the solid oral dosage form exhibits a dissolution profile comparable to the marketed esomeprazole delayed release granules for suspension wherein 0-5% of the esomeprazole is released in 0.1N HCl (300 ml) for 2 hours and at least 80% of the esomeprazole is released in phosphate buffer (pH 6.8; 1000 ml) using a USP II apparatus at 100 rpm for 30 minutes.

3. The solid oral dosage form of claim 1, wherein the suspension modifying inactive granulate is free of a binder.

4. The solid oral dosage form of claim 1, wherein the carrageenan of the inactive granulate is a gelling agent.

5. The solid oral dosage form of claim 4, wherein the carrageenan is within the granulate.

6. The solid oral dosage form of claim 1, wherein the gelling time of the dosage form is less than five minutes.

7. The solid oral dosage form of claim 1, wherein the gelling time of the dosage form is less than four minutes.

8. The solid oral dosage form of claim 1, wherein the dosage form is a free flowing mixture of the pellets and the granulate.

9. The solid oral dosage form of claim 1, wherein the pellets of esomeprazole magnesium are made in a process comprising the steps of:
(a) mixing the hydroxypropylmethyl cellulose and the polysorbate 80 with water;
(b) adding the esomeprazole magnesium to the mixture of step (a);
(c) coating the sugar spheres with the mixture of step (b);
(d) mixing the hydroxypropyl cellulose with water;
(e) mixing the talc and the magnesium stearate with water;
(f) adding the mixture of step (e) to the mixture of step (d) and mixing;
(g) applying the mixture of step (f) to the coated sugar spheres of step (c);
(h) adding the glycerol monostearate to water and mixing;
(i) adding the polysorbate 80 and the triethyl citrate to the mixture of step (h) and stirring;
(j) adding the methacrylic acid copolymer to the mixture of step (i); and
(k) coating the mixture of step (j) to the coated sugar spheres of step (g).

10. The solid oral dosage form of claim 1, wherein the suspension modifying inactive granulate is made in a process comprising the steps of:
(a) mixing the lactose/mannitol/dextrose, carrageenan, crospovidone, citric acid and iron oxide; and
(b) granulating the mixture of step (a) with a solvent to form the granulate.

11. A solid oral dosage form consisting of enteric coated pellets of esomeprazole magnesium and a suspension modifying inactive granulate, wherein:
the enteric coated pellets of esomeprazole magnesium consist of:
18.78% (w/w) of sugar spheres coated with a first layer, a second layer and an outermost third layer, and the first layer consists of 25.11% (w/w) esomeprazole magnesium, 1.7% (w/w) hydroxypropylmethyl cellulose and 0.5% (w/w) polysorbate 80;
the second layer consists of 9.03% (w/w) hydroxypropyl cellulose, 1.23% (w/w) magnesium stearate and 17.08% (w/w) talc over the first layer;
and the third outermost layer consists of 23.74% (w/w) methacrylic acid copolymer, 1.23% (w/w) glycerol monostearate, 0.13% (w/w) polysorbate 80 and 1.47% (w/w) triethyl citrate over the second layer, wherein the weight percentages are of the enteric coated pellets; and
the suspension modifying inactive granulate consists of 94.87% (w/w) dextrose, 2.5% (w/w) xanthan gum, 2.5% (w/w) crospovidone, 0.08% (w/w) citric acid and 0.05% (w/w) iron oxide, wherein the weight percentages are of the granulate.

12. The solid oral dosage form of claim 11, wherein the solid oral dosage form exhibits a dissolution profile comparable to the marketed esomeprazole delayed release granules for suspension wherein 0-5% of the esomeprazole is released in 0.1N HCl (300 ml) for 2 hours and at least 80% of the esomeprazole is released in phosphate buffer (pH 6.8; 1000 ml) using a USP II apparatus at 100 rpm for 30 minutes.

13. The solid oral dosage form of claim 11, wherein the suspension modifying inactive granulate is free of a binder.

14. The solid oral dosage form of claim 11, wherein the xanthan gum of the inactive granulate is a gelling agent.

15. The solid oral dosage form of claim 14, wherein the xanthan gum is within the granulate.

16. The solid oral dosage form of claim 11, wherein the gelling time of the dosage form is less than five minutes.

17. The solid oral dosage form of claim 11, wherein the gelling time of the dosage form is less than four minutes.

18. The solid oral dosage form of claim 11, wherein the dosage form is a free flowing mixture of the pellets and the granulate.

19. The solid oral dosage form of claim 11, wherein the pellets of esomeprazole magnesium are made in a process comprising the steps of:
(a) mixing the hydroxypropylmethyl cellulose and the polysorbate 80 with water;
(b) adding the esomeprazole magnesium to the mixture of step (a);
(c) coating the sugar spheres with the mixture of step (b);
(d) mixing the hydroxypropyl cellulose with water;
(e) mixing the talc and the magnesium stearate with water;
(f) adding the mixture of step (e) to the mixture of step (d) and mixing;
(g) applying the mixture of step (f) to the coated sugar spheres of step (c);
(h) adding the glycerol monostearate to water and mixing;
(i) adding the polysorbate 80 and the triethyl citrate to the mixture of step (h) and stirring;
(j) adding the methacrylic acid copolymer to the mixture of step (i); and
(k) coating the mixture of step (j) to the coated sugar spheres of step (g).

20. The solid oral dosage form of claim 11, wherein the suspension modifying inactive granulate is made in a process comprising the steps of:
(a) mixing the dextrose, xanthan gum, crospovidone, citric acid and iron oxide; and
(b) granulating the mixture of step (a) with a solvent to form the granulate.

\* \* \* \* \*